United States Patent [19]

Stapp

[11] 4,220,604
[45] * Sep. 2, 1980

[54] OXIDATIVE REARRANGEMENT OF OLEFINS

[75] Inventor: Paul R. Stapp, Bartlesville, Okla.

[73] Assignee: Phillips Petroleum Company, Bartlesville, Okla.

[*] Notice: The portion of the term of this patent subsequent to May 1, 1996, has been disclaimed.

[21] Appl. No.: 924,537

[22] Filed: Jul. 14, 1978

[51] Int. Cl.$^2$ ............................................. C07C 45/04
[52] U.S. Cl. ........................... 568/401; 560/174; 568/910; 568/900; 585/639
[58] Field of Search ............... 260/597 B, 593 R, 594

[56] References Cited

U.S. PATENT DOCUMENTS

| | | | |
|---|---|---|---|
| 3,154,586 | 11/1964 | Bander et al. | 260/597 B |
| 3,365,498 | 1/1968 | Bryant et al. | 260/597 B |
| 3,365,499 | 1/1968 | Clement et al. | 260/597 B |
| 3,668,257 | 6/1972 | Schaeffer | 260/597 B |
| 3,932,521 | 1/1976 | Gloyer et al. | 260/597 B |
| 3,944,623 | 3/1976 | Chabardes et al. | 260/597 B |
| 3,992,432 | 11/1976 | Napier et al. | 568/910 |
| 4,152,354 | 5/1979 | Stapp | 260/597 B |

*Primary Examiner*—Norman Morgenstern
*Assistant Examiner*—James H. Reamer

[57] ABSTRACT

An isoolefin is converted to a ketone, e.g., isobutylene to methyl ethyl ketone, by an oxidative rearrangement in a two-phase diluent system in the presence of free oxygen, a suitable surfactant, and a catalyst system comprising palladium, copper, and an alkali or alkaline earth metal chloride.

8 Claims, No Drawings

OXIDATIVE REARRANGEMENT OF OLEFINS

BACKGROUND OF THE INVENTION

This invention relates to the conversion of olefins to carbonyl compounds. In another aspect, this invention relates to a process for converting isoolefins to ketones. In another aspect, this invention relates to a process for converting isoolefins to ketones wherein the isoolefin undergoes an unusual carbon skeleton rearrangement. Another aspect of this invention relates to the conversion of an isoolefin into a ketone in the presence of a catalyst system comprising palladium, copper, and an alkali or alkaline earth metal chloride. This invention also relates to the conversion of an isoolefin in a diluent system comprised of at least two liquid phases with at least one being aqueous. In still another aspect, this invention relates to a process for converting isoolefins to ketones in the presence of a surfactant and a palladium, copper, and an alkali or alkaline earth metal chloride catalyst system.

The oxidation of olefins to carbonyl compounds in the presence of palladium group metal catalysts is well known. For example, in U.S. Pat. No. 3,154,586, ethylene is oxidized to acetaldehyde in the presence of palladium chloride, copper chloride, concentrated hydrochloric acid, and water. U.S. Pat. No. 3,154,586 also discloses the oxidation of isobutylene to isobutyraldehyde in the presence of palladium chloride, cupric bromide, oxygen, and water. These oxidations, however, generally occur without carbon skeleton rearrangement.

It is an object of this invention to provide a novel process for the conversion of isoolefins to ketones.

It is also an object of this invention to provide a process which subjects an isoolefin to oxidative rearrangement.

Another object of this invention is to provide a process for making methyl ethyl ketone from isobutylene.

Other objects, aspects, and advantages of this invention will be apparent to those skilled in the art upon a study of this disclosure and the appended claims.

SUMMARY OF THE INVENTION

The present invention provides a process for the conversion of isoolefins, e.g., isobutylene, to ketones, e.g., methyl ethyl ketone, which involves an unusual carbon skeleton rearrangement. An isoolefin is contacted with oxygen in a reaction diluent comprising at least two liquid phases, wherein at least one liquid phase is an aqueous phase, in the presence of a suitable surfactant and a catalyst comprising palladium, copper, and an alkali metal or alkaline earth metal chloride. A specific embodiment of this invention is the conversion of isobutylene to methyl ethyl ketone, which is an industrially valuable solvent. Generally, t-butyl alcohol is also formed as a reaction product, however, the alcohol can be separated and used as a solvent or can be dehydrated to isobutylene for recycle to the oxidation reaction zone.

DETAILED DESCRIPTION OF THE INVENTION

I. Isoolefin Reactant

For purposes of this invention, an isoolefin can be defined as a 1,1 disubstituted ethylene compound. The substituted groups of the ethylene compound can be taken together to form a cyclic system thus forming a methylene carbocyclic compound.

The isoolefin reactant which is utilized according to the process of this invention can be referred to as the olefinic reactant and can be any suitable isoolefin, generally, however, the isoolefin reactant contains from 4 to about 30 carbon atoms per molecule and can be represented by the following general formula I:

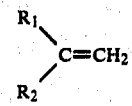

wherein each of $R_1$ and $R_2$ is independently selected from the groups consisting of alkyl radicals containing from 1 to about 20 carbon atoms per radical and cycloalkyl radicals containing from 5 to 20 carbon atoms per radical, and wherein $R_1$ and $R_2$ can be taken together to form an alkylene or cycloalkylene radical thus forming a cyclic system containing from about 3 to about 20 carbon atoms per ring. In addition, $R_1$ and $R_2$ can contain one or more or combinations of substituents that are substantially inert to the conditions of the reaction such as aryl, halogen, ester, and the like.

The preferred reactants for the process of this invention are those in which both $R_1$ and $R_2$ of general formula I are alkyl radicals containing from 1 to about 8 carbon atoms per radical.

For reasons of availability and cost and for value of the resulting products the currently most preferred reactants for the process of this invention are those of general formula I wherein each of $R_1$ and $R_2$ are selected from alkyl radicals containing from 1 to about 3 carbon atoms per radical.

Specific examples of suitable reactants include isobutylene, 2-methyl-1-butene, 2-propyl-1-pentene, 2-ethyl-1-butene, 2-methyl-1-octene, isopropenylcyclohexane, methylenecyclobutane, methylenecyclohexane, methylenecyclododecane, 2-methyl-3-phenyl-1-propene, 2-methyl-4-chloro-1-butene, ethyl 3-methyl-3-butenoate, and the like.

II. Catalyst System

The catalyst utilized according to the instant invention for the oxidation of olefinic reactants to carbonyl compounds is made up of three components: (1) a palladium component, (2) a copper component, and (3) an alkali metal or alkaline earth metal chloride component.

(1) Palladium Component

The palladium component of the catalyst system can be palladium metal such as finely divided palladium powder or a palladium compound. Examples of suitable palladium compounds include allyl palladium chloride dimer $[C_3H_5PdCl]_2$, dichlorobis(triphenylphosphine)palladium(II), palladium(II) acetate, palladium(II) acetylacetonate, tetrakis(triphenylphosphine)palladium(O), palladium(II) chloride, palladium(II) iodide, palladium(II) nitrate, and the like. Mixtures of the above palladium compounds can also be utilized as the palladium component of the instant catalyst system is so desired.

(2) Copper Component

The copper component of the catalyst system can be provided by utilizing a cuprous or cupric compound or mixture thereof. A wide variety of copper compounds can be utilized to provide the copper component of the instant catalyst system. Specific examples of suitable copper compounds include copper(I) acetate, copper(II) acetylacetonate, copper(I) bromide, copper(I) chloride, copper(II) chloride, copper(II) nitrate, and the like. Mixtures of suitable copper compounds can also be employed to provide the copper component of the instant catalyst system if so desired.

(3) Alkali Metal or Alkaline Earth Metal Chloride

The third component of the catalyst system is a chloride of an alkali metal or an alkaline earth metal. Specific examples of suitable alkali metal chlorides include lithium chloride, sodium chloride, potassium chloride, rubidium chloride, and cesium chloride. Examples of suitable alkaline earth metal chlorides include calcium chloride, barium chloride, strontium chloride, magnesium chloride, and beryllium chloride. Mixtures of the above metal chlorides can be employed as the third component of the catalyst system if so desired.

The ratios of the various catalyst components can be expressed in terms of molar ratio of copper to palladium and a molar ratio of chloride ion derived from the alkali metal or alkaline earth metal chloride to palladium. The molar ratio of copper component to palladium component in the instant catalyst system is broadly from about 1/1 up to about 200/1 and preferably from about 2/1 up to about 50/1. The molar ratio of chloride ion derived from the alkali metal or alkaline earth metal chloride to palladium is broadly from about 2/1 to about 1,000/1 and preferably from about 5/1 up to about 400/1.

The amount of catalyst employed according to the instant invention can be expressed in terms of the molar ratio of olefinic reactant to palladium component of the catalyst system. Broadly, the molar ratio of olefinic reactant to palladium component is from about 5/1 up to about 1,000/1 and preferably from about 10/1 up to about 250/1.

Another component of the reaction system according to this invention is a compound with surface-active properties, i.e., a surfactant. Although any suitable surfactant can be utilized, it is generally preferred that the surfactant be chosen from one of the five following groups:

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms. It will be noted that a variety of anions are suitable as the $X^-$ component of the quaternary ammonium salts, but it is believed that hydroxide ion and alkoxide ions are not suitable as the anion component of the quaternary ammonium compounds. Specific examples of quaternary ammonium salts according to the general formula given above include cetyltrimethylammonium bromide (hexadecyltrimethylammonium bromide), tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutylammonium fluoride, tetrabutylammonium tetrafluoroborate, and the like.

(B) Alkali metal alkyl sulfates of the general formula $R'^vOSO_3M$ wherein $R'^v$ is an alkyl radical of from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and the like.

(C) Alkali metal salts of alkanoic acids of the general formula $R'^vCO_2M$ wherein $R'^v$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and the like.

(D) Alkali metal salts of alkaryl sulfonic acids of the general formula

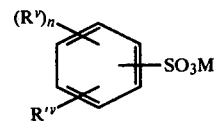

wherein $R'^v$ and M have the same meaning as given above and wherein $R^v$ is an alkyl radical of 1 to 4 carbon atoms and wherein n is 0 or an integer of from 1 to 4. Specific examples of compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzene sulfonate, sodium eicosylbenzenesulfonate, potassium dodecyltoluenesulfonate, sodium dodecylxylenesulfonate, and the like.

(E) 1-Alkyl pyridinium salts of the general formula

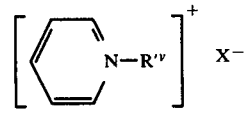

wherein $R'^v$ and $X^-$ have the same meaning as described above. Examples of suitable 1-alkyl pyridinium salts include 1-dodecylpyridinium para-toluenesulfonate, 1-dodecylpyridinium chloride, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio surfactant to palladium compound will be from 0.01/1 to 10/1 and preferably from 0.1/1 to 3/1.

III. Diluent System

The oxidation of the olefinic reactant according to the instant invention is carried out in the presence of a diluent comprised of at least two liquid phases (preferably only two), at least one of which is an aqueous phase.

The nonaqueous phase will hereinafter be termed the organic phase. Said organic phase should be relatively inert to the oxidation conditions, of course, and also relatively inert to hydrolysis-type reactions. Furthermore, it is apparent that if at least two phases are present, at least one of which is an aqueous phase, that the organic diluent utilized must have somewhat limited solubility in the aqueous phase. Within these general requirements, a rather broad range of organic compounds can be utilized to form the organic phase according to the instant invention. Generally speaking, suitable compounds can be found in the classes of compounds described as alkanes, cycloalkanes, aromatic hydrocarbons, alkyl-substituted aromatic hydrocarbons, halogenated aromatic compounds, and esters of aromatic carboxylic acids although the latter may be less preferred because of a tendency toward hydrolysis of the ester group in certain instances. In addition, it is believed that compounds such as nitrobenzene and benzonitrile, commonly utilized as solvents for many organic reactions, would show an inhibitory effect on the reaction of the instant invention presumably by complexing of one or more catalyst components. Specific examples of suitable organic diluents include cyclohexane, hexane, benzene, toluene, chlorobenzene, methylbenzoate, bromobenzene, 1,2,4-trichlorobenzene, ortho-dichlorobenzene, sulfolane, orthoxylene, para-xylene, meta-xylene, methylcyclopentane, dimethyl orthophthalate, and the like. Mixtures of the above organic diluents may be utilized in some cases as desired. Generally speaking, the choice of the organic diluent may be often determined based on the difference in boiling points expected between the product of the oxidation reaction and the organic diluent so as to facilitate separation of the components of the reaction mixture.

The amounts of aqueous phase and organic diluent phase based on the starting olefinic reactant can vary over a wide range and suitable broad range includes from about 50 to about 1,000 ml of organic diluent per mole of olefinic reactant. Similarly, the broad range for the amount of aqueous phase is from about 50 to about 1,000 ml per mole of olefinic reactant and preferably from about 100 to about 500 ml per mole of olefinic reactant. It is worth pointing out some predictions relating to the expected effects of the volume of aqueous phase on the oxidation reaction of the instant invention. First, if the aqueous phase volume becomes too small, the concentration of the catalyst components in the aqueous phase may cause a salting-out effect on the olefinic reactant thus greatly slowing down the reaction rate wherein the olefinic reactant is oxidized to the desired carbonyl compound. Secondly, if the aqueous phase becomes too large, the concentration of catalyst components may be so dilute that the reaction with the olefinic reactant may also be greatly slowed. However, it can be seen that a judicious choice of the optimum amount of the aqueous phase for high conversion levels of the olefinic reactant can readily be determined by a few well-chosen experiments.

At present, it is believed that the primary function of the organic phase in the reaction system of the instant invention is to increase the selectivity to the desired carbonyl compound by effectively removing the carbonyl compound product from the locus of the oxidation reaction thereby preventing side reactions such as isomerization and/or further oxidation of the carbonyl compound. However, this explanation is to be treated merely as a theory of the mode of action of the organic phase in the reaction and the instant invention should not be bound to any extent by said theory.

IV. Oxygen

As indicated previously, the reaction of the instant invention is an oxidation reaction whereby an olefinic reactant is converted to a carbonyl compound in the presence of a catalyst and diluent system described above. Thus, the reaction of the instant invention is carried out in the presence of free oxygen. The oxygen can be supplied to the reaction mixture essentially as pure oxygen or admixed with other gases which are essentially inert to the reaction conditions. Air can be utilized as a source of oxygen for the oxidation reaction of this invention. As is generally true for most oxidation reactions, the reaction of the instant invention can be exothermic and thus some care should be exercised in the amount of oxygen present in the reaction system. For this reason and also to improve control of the temperature of the reaction, it is preferred to add oxygen or the gaseous mixture containing oxygen to the reaction zone incrementally such that explosive ranges of oxygen concentration do not develop. The pressure of oxygen utilized for the instant invention can broadly be from 2 up to 250 psig and preferably from 10 to 100 psig above the autogenous pressure at the temperature utilized.

V. Reaction Conditions

The temperature utilized in the instant invention is broadly from 20-200° C. and preferably from 60-150° C. It is to be noted, however, that the particular temperature employed is dependent somewhat on the olefinic reactant. For example, at relatively high temperatures, a lower molecular weight olefinic reactant can tend to be very insoluble in the aqueous phase of the two-phase system of the instant invention, thus causing a reduced conversion of the olefinic reactant. On the other hand, a higher molecular weight olefinic reactant can tolerate a higher reaction temperature and still maintain a reasonable degree of solubility in the aqueous phase and thus achieve a good degree of conversion at the higher temperature.

The time employed for the reaction according to the instant invention can vary over a wide range and will to some extent depend on the desired degree of conversion of the olefinic reactant. Generally, a time period such as from 30 minutes to eight hours will be employed in the instant invention.

Because the oxidation reaction according to the instant invention is carried out in the presence of a diluent system comprising at least two liquid phases, it is expected that good stirring will be of benefit and conventional means of achieving good agitation and contact between the liquid phases can be employed as taught by the prior art.

The charge order of the reaction components and catalyst components is not particularly critical in the process of the instant invention. However, the presence of oxygen in the reaction mixture prior to heating of the mixture to the desired reaction temperature is generally preferred.

The process of the instant invention can be carried out in either a batch or continuous process.

Reaction vessels utilized in the process of the instant invention should, of course, be able to withstand the oxidizing conditions which are present. For this reason, glass-lined, tantalum, or titanium clad vessels and conduits are recommended for use in the process of this invention.

VI. Reaction Mixture Workup

A variety of methods can be utilized to recover the products, unreacted olefinic starting materials, and the catalyst in the aqueous phase in the instant invention. For example, the reaction mixture can be admixed with a saturated aqueous sodium chloride solution followed by extraction of the mixture into diethyl ether. The ether extract can then be distilled or treated in such a manner as to remove the ether leaving the organic residue containing the product and any unreacted olefinic reactant. Said residue can them be subjected to fractional distillation procedures to recover the various components.

Another method of reaction mixture workup involves fractional distillation of the entire reaction mixture to separate the components into various fractions with recycle of the distillation kettle bottoms to the reaction zone as that portion contains essentially all of the catalyst system for the reaction.

Another method of treating the reaction mixture is to contact the entire mixture with a lower alkane such as n-pentane and then separate the aqueous phase from the organic phase. This can be followed by fractional distillation of the organic phase to recover the products and any unreacted olefinic reactants. The aqueous phase can be recycled to the reaction zone as described above since it contains essentially all of the catalyst components.

Still another method of the reaction mixture workup is to contact the organic product mixture obtained from the ether or pentane extractions described above with a dehydrating agent, such as alumina, to convert any alcohol product to an olefin product. The resulting mixture can be fractionally distilled to recover the oxidation products and the olefin for recycle to the oxidation reaction zone.

VII. Product Utility

As indicated earlier, the reaction of the instant invention provides a process for the conversion of olefinic reactants to carbonyl compounds. For example, isobutylene can be oxidized to methyl ethyl ketone which is an industrially valuable solvent. Another product of this reaction is t-butyl alcohol which can be utilized as a solvent or can be dehydrated to isobutylene for recycle to the oxidation reaction zone.

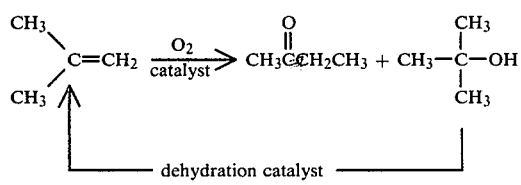

It is seen that the oxidation product is formed by migration of one of the groups $R_1$ and $R_2$ of Formula I. When $R_1$ and $R_2$ are equivalent, only one oxidative rearrangement product is formed. However, when $R_1$ and $R_2$ are different, two oxidative rearrangement products would be expected.

The following examples are set forth as illustrative of the process of this invention and are not meant to be restrictive.

VIII. Examples

In the runs that are described in the following examples, the reaction vessel utilized in each of the runs was a 250 ml Fischer-Porter aerosol compatibility bottle equipped with a magnetic stirrer. Generally, the bottle was charged with the catalyst system, the diluents and the isobutylene reactant after which the bottle was placed in an oil bath, pressured to about 30 psig with oxygen and then heated to the desired temperature. During the reaction period, the bottle was pressured intermittently at about 10–30 minute intervals to an oxygen pressure of about 80–120 psig. Usually the reaction mixture was recovered from the bottle reactor by cooling the reactor, venting the gas phase through a cold trap to collect unreacted isobutylene and pouring the mixture into abut 100 ml of saturated sodium chloride solution. This mixture was then continuously extracted with diethyl ether for 24 hours. The ether extract was washed with water and dried over magnesium sulfate. The dried ether extract was then filtered and the ether stripped off in a distillation step. The residue remaining after the removal of the ether was then analyzed by gas-liquid chromatography (glc). Significant deviations from the above general procedures will be noted where appropriate in the respective examples that follow.

EXAMPLE I

The 250 ml Fischer-Porter aerosol compatibility bottle was charged with palladium chloride (5 mmoles), cupric chloride dihydrate (20 mmoles), lithium chloride (200 mmoles), hexadecyltrimethylammonium bromide (1.8 mmoles), water (50 ml), chlorobenzene (50 ml), and isobutylene (212.5 mmoles). The reactor was pressured to 30 psig (207 kPa) and heated to 105° C. The reaction was continued for about six hours with intermittent pressuring with oxygen as described above. Analysis of the residue from the ether distillation by glc indicated that the product contained methyl ethyl ketone (43.2 mmoles), t-butyl alcohol (58.8 mmoles), isobutyraldehyde (7 mmoles, 3-chloro-2-butanone (6.5 mmoles), t-butyl isobutyrate (6.8 mmoles), and acetone (trace).

The results of this run demonstrate operability of the present invention for the conversion of isobutylene to methyl ethyl ketone.

EXAMPLE II

A series of runs was carried out to show the effect of the alkali metal chloride on the oxidative rearrangement of isobutylene. In each run, the reactor was charged with palladium chloride (5 moles), cupric chloride dihydrate (20 mmoles), hexadecyltrimethylammonium bromide (1.8 mmoles), water (50 ml), chlorobenzene (50 ml), isobutylene (various amounts), and lithium chloride (various amounts). The runs were carried out using the procedure described above at a reaction temperature of 105° C. for a reaction time of 5–6 hours. The results of these runs are shown in Table I.

TABLE I

| Run[a] No. | LiCl, mmoles | Isobutylene, mmoles | Isobutylene Conversion Mole Percent | Product Mixture | | |
|---|---|---|---|---|---|---|
| | | | | Methyl Ethyl Ketone mmoles | t-BuOH, mmoles | Acetone, mmoles |
| 1 | None | 196.4 | (b) | 0 | 108 | 4 |
| 2 | 50 | 196.4 | 57 | 12.1 | 56 | 9 |
| 3 | 100 | 198.2 | 50 | 23 | 48 | 11 |
| 4 | 200 | 207.1 | 87 | 47 | 29 | 16 |
| 5 | 300 | 196.4 | 60 | 30 | 38 | 9 |

[a]Run 4 was carried out for six hours. The other runs were carried out for about five hours.
[b]Not determined.

The results of these runs show that no detectable amount of methyl ethyl ketone was formed under these reaction conditions in the absence of lithium chloride (Run 1). Methyl ethyl kethone was formed in the presence of 50 to 300 mmoles of lithium chloride (Runs 2 to 5).

These runs show that the presence of lithium chloride is required for the formation of methyl ethyl ketone from isobutylene and that the lithium chloride is effective over a wide range of concentrations.

Reasonable variations and modifications are possible within the scope of the foregoing disclosure and the appended claims to the invention.

I claim:

1. A process for the conversion of an isoolefin reactant to a ketone which comprises contacting:
   (a) an isoolefin which has the general formula:

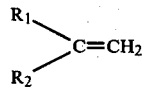

wherein $R_1$ and $R_2$ are alkyl radicals containing from 1 to about 8 carbon atoms per radical with
   (b) oxygen in
   (c) a reaction diluent comprising at least two liquid phases wherein at least one liquid phase is an aqueous phase, in the presence of
   (d) a catalyst comprising palladium, copper, and an alkali metal or alkaline earth metal chloride, and
   (e) a surfactant, wherein said surfactant is selected from the group consisting of:
   (1) quaternary ammonium salts of the general formula

(2) alkali metal alkyl sulfates of the general formula $R'^{v}OSO_3M$,
   (3) alkali metal salts of alkanoic acids of the general formula $R'^{v}CO_2M$,
   (4) alkali metal salts of alkaryl sulfonic acids of the general formula

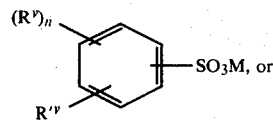

(5) 1-alkyl pyridinium salts of the general formula

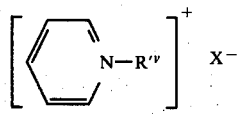

wherein $R'''$ is an alkyl radical of from 1 to 20 carbon atoms and wherein the total number of carbon atoms in said quaternary ammonium salt is from about 8 to about 30 carbon atoms; $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms; $R'^{v}$ is an alkyl radical of from 10 to about 20 carbon atoms; M is an alkali metal; $R^v$ is an alkyl radical of 1 to 4 carbon atoms and wherein n is 0 or an integer of from 1 to 4,
   under such reaction conditions that the isoolefin undergoes oxidative rearrangement to a ketone.

2. The process of claim 1 wherein $R_1$ and $R_2$ are alkyl radicals containing from 1 to about 3 carbon atoms per radical.

3. The process of claim 1 wherein:
   the molar ratio of copper to palladium is about 1:1 to about 200:1;
   the molar ratio of the chloride ion derived from the alkali metal or alkaline earth metal chloride to palladium is about 2:1 to about 1,000:1;
   the molar ratio of the isoolefinic reactant to palladium is about 5:1 to about 1,000:1;
   the molar ratio of said surfactant to palladium is about 0.01:1 to about 10:1;
   the pressure of oxygen in the reaction system is in the range of from about 2 to about 250 psig above the autogenous pressure at the temperature utilized; and
   said reaction temperature is in the range of about 20° C. to about 200° C.

4. The process of claim 1 wherein the diluent consists of two phases, one aqueous and the other an organic phase wherein said organic phase is relatively inert to the oxidation conditions employed, inert to hydrolysis-type reactions, and shows a limited solubility in the aqueous phase.

5. The process of claim 4 wherein the amount of organic diluent is in the range of about 50 to about 1000 ml of organic diluent per mole of isoolefinic reactant and the amount of aqueous phase is in the range of about 50 to about 1000 ml of aqueous phase per mole of isoolefinic reactant.

6. The process of claim 1 wherein said isoolefinic reactant is isobutylene and the ketone formed is methyl ethyl ketone.

7. The process of claim 6 wherein:
   the reaction diluent is an aqueous phase and an organic phase with the organic phase being chlorobenzene;
   the catalyst is palladium chloride, cupric chloride, and lithium chloride; and
   the surfactant is hexadecyltrimethylammonium bromide.

8. The process of claim 6 wherein t-butyl alcohol is also a reaction product with said t-butyl alcohol being subjected to dehydration in order to form isobutylene which is then recycled to the oxidation reaction zone.

* * * * *